United States Patent [19]

Yamada et al.

[11] 4,061,748
[45] Dec. 6, 1977

[54] 7-(α-(4-HYDROXY-1,5-NAPHTHYRIDINE-3-CARBONAMIDO)-α-PHENYLACETAMIDO) CEPHALOSPORIN DERIVATIVES

[75] Inventors: Hirotada Yamada, Nishinomiya; Kosaku Okamura, Takarazuka; Hisao Tobiki, Kobe; Norihiko Tanno, Ashiya; Kozo Shimago, Toyonaka; Takenari Nakagome, Nishinomiya; Toshiaki Komatsu, Takarazuka; Akio Izawa, Kawanishi; Hiroshi Noguchi, Maebashi; Kenji Irie, Takarazuka; Yasuko Eda, Toyonaka, all of Japan

[73] Assignee: Sumitomo Chemical Company, Limited, Osaka, Japan

[21] Appl. No.: 674,205

[22] Filed: Apr. 5, 1976

[30] Foreign Application Priority Data

Apr. 3, 1975 Japan .................................. 50-41011

[51] Int. Cl.² .................. A61K 31/545; C07D 501/36
[52] U.S. Cl. ...................................... 424/246; 544/27; 544/22
[58] Field of Search ...................... 260/243 C; 424/246

[56] References Cited
U.S. PATENT DOCUMENTS 3,954,802  5/1976  Kocsis et al. ..................... 260/243 C Primary Examiner—Nicholas S. Rizzo
Attorney, Agent, or Firm—Sughrue, Rothwell, Mion, Zinn and Macpeak

[57] ABSTRACT

A cephalosporin derivative of formula (I):

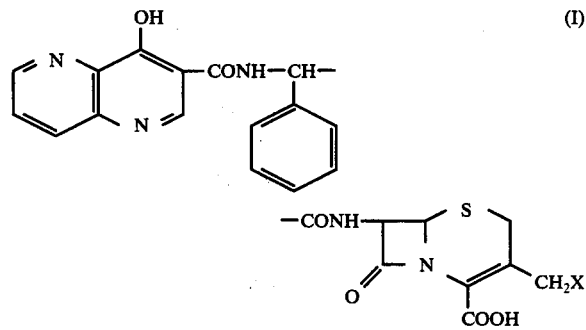

wherein X is an —OCOCH₃ group or an -S-Het group in which Het is a 5- or 6-membered heterocyclic ring containing one to four hetero atoms selected from the group consisting of nitrogen, oxygen and sulfur atoms, which may be substituted with one or more substituents, and the non-toxic pharmaceutically acceptable salts thereof which are useful as an antimicrobial material and which are prepared by the reaction of a compound of formula (II):

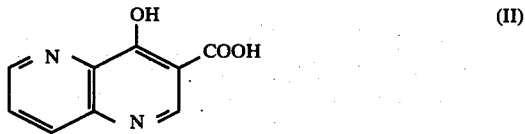

or a reactive derivative thereof, with a compound of formula (III):

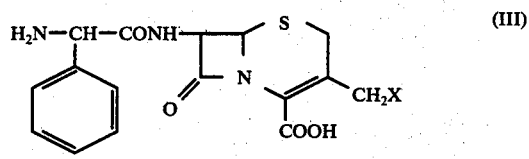

wherein X is as defined above, or a derivative thereof.

6 Claims, No Drawings

7-(α-(4-HYDROXY-1,5-NAPHTHYRIDINE-3-CARBONAMIDO)-α-PHENYLACETAMIDO) CEPHALOSPORIN DERIVATIVES

BACKGROUND OF THE INVENTION

1. Field of the Invention

The present invention relates to novel cephalosporins and to a process for the preparation thereof. More particularly, it relates to novel cephalosporins of formula (I):

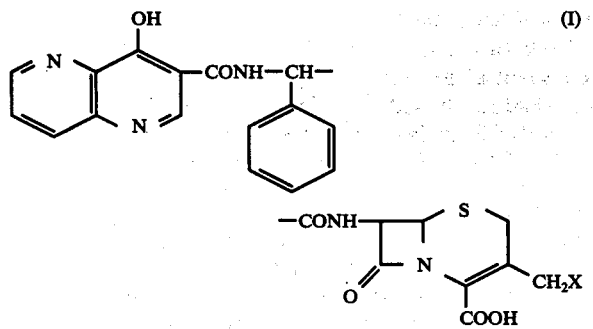

wherein X is as described hereinafter, the non-toxic pharmaceutically acceptable salts thereof and to the preparation thereof.

2. Description of the Prior Art

It is known that cephalosporin series compounds such as Cephalothin and Cefazolin are very effective and are widely used as chemotherapeutic agents for infectious diseases caused by gram-positive or gram-negative bacteria.

However, these cephalosporin series compounds have no effect on infectious diseases caused by *Pseudomonas aeruginosa* which have been increasingly spreading in recent years, and are often very difficult to cure. Cephalosporin series compounds which are effective against *Pseudomonas aeruginosa* are not yet commercially available.

In Japanese patent application (OPI) No. 35,392/1974, Belgian Pat. No. 808,906, Japanese patent application (OPI) No. 70,990/1974 and in Japanese patent application (OPI) Nos. 87,694/1974, and 82,687/1974, some cephalosporins are disclosed with antibacterial activity against gram-positive and gram-negative bacteria, including *Pseudomonas*.

SUMMARY OF THE INVENTION

In one embodiment, the present invention provides compounds of formula (I):

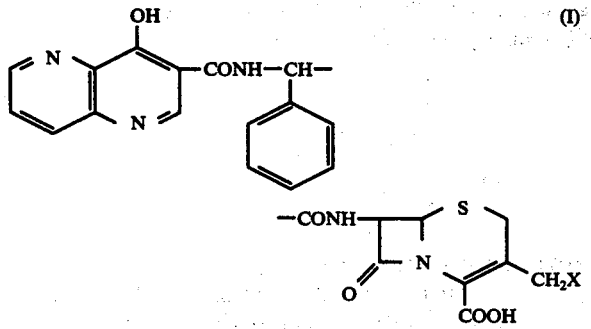

wherein X is an —OCOCH$_3$ group or an —S-Het group in which Het is a 5- or 6-membered heterocyclic ring containing one to four hetero atoms selected from the group consisting of nitrogen, oxygen and sulfur atoms which, may be substituted with one or more substituents, and the non-toxic pharmaceutically acceptable salts thereof.

In another embodiment, this invention provides a pharmaceutical composition containing at least one compound of formula (I) or a non-toxic pharmaceutically acceptable salt thereof (I) as an active ingredient.

In a further embodiment, this invention provides a process for the preparation of compounds of formula (I) and the non-toxic pharmaceutically acceptable salts thereof.

DETAILED DESCRIPTION OF THE INVENTION

As a result of various studies, it has been found that the cephalosporins of formula (I) exert a strong antimicrobial activity against gram-positive and gram-negative bacteria, have desirable pharmacokinetic properties and are useful as antimicrobial agents for infectious diseases in animals, including human beings, poultry and cattle.

The compounds of formula (I) above, for example, display a noticeable antimicrobial activity against bacteria to which known cephalosporins series compounds are hardly effective such as *Pseudomonas aeruginosa*, indole positive Proteus, Serratia and *Enterobacter aerogeneus*.

The compounds of formula (I) further show a stronger antibacterial activity in vitro and in vivo against various pathogenic organisms as well as better pharmacokinetic properties, such as higher serum concentrations, as compared with known cephalosporins, for example, 7-[D-2-(4-hydroxyquinoline-3-carbonamido)-2-phenylacetamido] cephalosporanic acid and 7-[D-2-(4-hydroxypyridine-3-carbonamido)-2-phenylacetamido] cephalosporanic acid, which are disclosed in Japanese patent application (OPI) Nos. 35,392/1974 and 82,687/1974.

In formula (I), X is an —OCOCH$_3$ group or an —S-Het group wherein —Het is a 5- or 6-membered heterocyclic ring containing one to four hetero atoms selected from the group consisting of nitrogen, oxygen and sulfur atoms. The heterocyclic ring may be substituted with a (C$_1$-C$_4$) alkyl group, a hydroxy group, a lower alkoxy group, a mercapto group or a hydroxymethyl group. Examples of suitable heterocyclic rings include 1-methyl-tetrazol-5-yl, 2-methyl-1,3,4-thiadiazol-5-yl, 1,2,3-triazol-5-yl, 1,2,4-triazol-3-yl, tetrazol-5-yl, 2-methyltetrazol-5-yl, 2-mercapto-1,3,4-thiadiazol-5-yl, 2-hydroxymetyl-1,3,4-oxadiazol-5-yl, 2-hydroxymethyl-1,3,4-thiadiazol-5-yl, 2-aminomethyl-1,3,4-thiadiazol-5-yl, 3-hydroxypyridazin-6-yl, 1,3,4-thiadiazol-5-yl, 2-methylamino-1,3,4-thiadiazol-5-yl and the like.

Examples of non-toxic pharmaceutically acceptable salts derived from the compounds of formula (I) include the sodium salt, the potassium salt, the calcium salt, the magnesium salt, the triethylamine salt, the diethanolamine salt, the morpholine salt, the procaine salt, the L-arginine salt, the L-lysine salt and the like.

The α-carbon atom of the side chain (phenylglycine moiety) attached to the 7-position of the compounds of formula (I) is an asymmetric carbon atom, and, therefore, two optically active isomers exist. These two isomers (D-diastereomer and L-diastereomer) and the DLform are included within the scope of the present invention, but the D-diastereomer is preferred.

The compounds of formula (I) of the present invention can be prepared by reacting a carboxylic acid of formula (II):

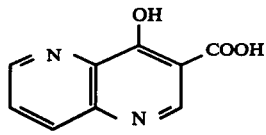

or a reactive derivative thereof, with a compound of formula (III):

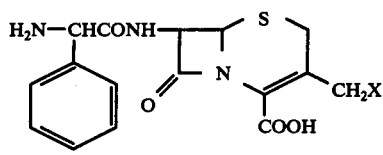

wherein X is as defined above, or a salt or derivative thereof, and when X is an —OCOCH₃ group, by further reacting the resulting product with a compound of the formula SH-Het, in which Het is as defined above, to convert X into an —S-Het group, if necessary.

Referring more particularly to the process, inert solvents which can be used in the reaction between the compounds of formulae (II) and (III) include polar solvents such as dichloromethane, chloroform, acetone, tetrahydrofuran, dioxane, acetonitrile, methyl isobutyl ketone, ethyl alcohol, dimethylformamide, dimethylacetamide, dimethyl sulfoxide, nitromethane, hexamethylphosphoric triamide, sulfolane, and the like; non-polar solvents such as benzene, toluene, petroleum ether, n-hexane and the like; and mixtures thereof. These solvents can be used in combination with water, if desired.

The reactive derivatives of the compounds of formula (II) include reactive derivatives of a carboxyl group, for example, an acid halide, an acid anhydride, an acid azolide, an active ester, an acid azide and the like. Referring more particularly to these reactive derivatives, examples include mixed acid anhydrides or symmetric acid anhydrides with acids such as dialkyl phosphoric acids, phenyl phosphoric acid, diphenyl phosphoric acid, dibenzyl phosphoric acid, halogenated phosphoric acids, dialkyl phosphorous acids, methanesulfonic acid, toluenesulfonic acid, naphthalenesulfonic acid, alkylcarbonates, aliphatic carboxylic acids (for example, pivalic acid, pentanoic acid, isopentanoic acid, 2-ethylbutanoic acid); acid azolides with imidazole, substituted imidazoles, dimethylpyrazole, triazole, and the like; and active esters such as cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, p-nitrophenylthio ester, carboxymethylthio ester, pyridyl ester, piperidyl ester, 8-quinolylthio ester, and esters with 1-hydroxy-2(1H)-pyridone, N-hydroxysuccinimide or N-hydroxyphthalimide.

Further, when the compounds of formula (II) are used in the form of the free acid (or a salt thereof), it is preferred to carry out the reaction in the presence of coupling agents such as N,N'-dicyclohexylcarbodiimide, N-cyclohexyl-N-morpholinoethylcarbodiimide, N-cyclohexyl-N-(4-diethylaminocyclohexyl)carbodii-mide, N,N'-diethylcarbodiimide, N,N'-diisopropylcarbodiimide, N-ethyl-N-(3-dimethylaminopropyl)carbodiimide, N,N'-carbonyldi-(2-methylimidazole), pentamethyleneketene-N-cyclohexylimine, diphenylketene-N-cyclohexylimine, 2-ethyl-7-hydroxybenzisoxazolium salt, N-ethyl-5-phenylisoxazolium-4'-sulfonate monohydrate (chloromethylene)dimethyl ammonium chloride and the like.

As described above, those amidating agents which are generally used in the fields of peptide chemistry, penicillin chemistry and cephalosporin chemistry can be used in the present invention.

Examples of the salts of compounds of formula (III) include an alkali metal salt or an alkaline earth metal salt (for example, the sodium, potassium, calcium, etc., salts) of acids of formula (III); organic amine salts (for example, trimethylamine, triethylamine, quinoline, collidine, etc., salts) of the acids of formula (III); and organic sulfonic acid salts (for example, toluenesulfonic acid, naphthalenesulfonic acid, tetralinsulfonic acid, etc., salts) of the acids of formula (III). Examples of derivatives of compounds of formula (III) include carboxyl derivatives in which the carboxyl group is protected by esterification or amidation, or is in the form of the anhydride thereof.

The carboxyl-protecting group can be removed after the acylation reaction under mild conditions, for example, by a solvolysis such as a hydrolysis or an alcoholysis, a catalytic hydrogenation, a reduction, an oxidation, a nucleophilic substitution reaction, a photochemical reaction or an enzymatic reaction.

Examples of groups formed by suitable carboxyl-protecting groups include a silyl ester, an organo-tin ester, a toluenesulfonyl ethyl ester, a p-nitrobenzyl ester, a benzyl ester, a phenacyl ester, a 2-furylmethyl ester, a diphenylmethyl ester, a substituted diphenylmethyl ester, a p-methoxybenzyl ester, a trityl ester, a benzoyloxymethyl ester, a lower alkanoyl oxymethyl ester, a dimethylmethyleneamino ester, a p-nitrophenyl ester, a methylsulfonylphenyl ester, a methylthiophenyl ester, a t-butyl ester, a 4-picolyl ester, an iodoethyl ester, a trichloroethyl ester, a phthalimidomethyl ester, a 3,4-dimethoxy or 3,5-dimethylbenzyl ester, a 2-nitrobenzyl ester, a 2,2'-dinitrodiphenyl ester, an acetyloxycarbonyl group, a trichloroethyl ester, a

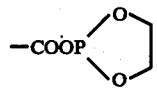

group, a —COON=CHR' group (in which R' is an alkyl group or an aryl group),

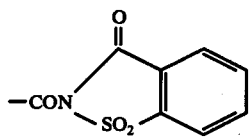

group and the like, which are formed from carboxyl-protecting groups conventionally used in the fields of peptide, penicillin and cephalosporin chemistry.

In case of the silyl ester, other substituents of the compound of formula (III), if any, such as a hydroxy group or an amino group may be silylated.

In case of these derivatives of compounds of formula (III), their hydrochloric acid, p-toluenesulfonic acid, naphthalene sulfonic acid or tetralin sulfonic acid salts may also be used.

The reaction between the acid represented by formula (II) or a reactive derivative thereof and a 7-α-amino-acylamidocephalosporin represented by formula (III) or a derivative thereof can be carried out at any temperature, usually below about 50° C.

Furthermore, the compounds of formula (I) where X is S-Het of the present invention can also be prepared by reacting an N-acylamino-α-phenylacetamido-cephalosporin of formula (IV):

(IV)

with a thiol represented by formula (V):

HS—Het      (V)

wherein Het is as defined above.

Various known methods (as described in Japanese patent publication Nos. 12,136/1971, 2,340/1971, 14,734/1971, Japanese patent application (OPI) No. 68,593/1973 and *Journal of the Chemical Society*, 1965, 5015) can be used for this reaction.

Further, the compounds of formula (I) where X is —S-Het can also be prepared by reacting an N-acylamino-α-phenylacetamido cephalosporin of formula (VIII):

(VIII)

wherein Y is a halogen atom or

R is H or a carboxyl-protecting group as is commonly used, with a thiol represented by formula (V):

HS—Het      (V)

wherein Het is as defined above.

Further, another method for the preparation of compounds of formula (I) comprises reacting an acylamino carboxylic acid of formula (VI):

(VI)

or a reactive derivative thereof, with a compound of formula (VII):

(VII)

wherein X is as defined above, or a derivative thereof, and when X is an —OCOCH$_3$ group, further reacting the resulting reaction product, if necessary, with a heterocyclic thiol of formula (V):

HS—Het      (V)

in which Het is as defined above.

The compounds of formula (III) can easily be prepared by the methods which disclosed in, for example, U.S. Pat. Nos. 3,634,416 and 3,634,418, Dutch Pat. No. 70/05519, Japanese patent application (OPI) No. 12,579/1972, and *Journal of Medicinal Chemistry* 9 (5) 746 (1966).

The compounds of general formula (I) can be administered intramuscularly or intravenously, for example, in the form of a solution, a suspension and the like.

Compositions or preparations containing one or more compounds of general formula (I) as an active ingredient(s) can be prepared by admixing the compound(s) of formula (I) with one or more pharmaceutically acceptable carriers or diluents such as water.

A usual dosage of the compounds of formula (I) is about 400 mg to about 20 g/day, preferably about 500 mg to 4 g/day, in single or multiple doses, generally multiple doses, for an adult (about 60 kg of body weight).

The following examples illustrate the preparation of compounds of the invention but are not to be construed as limiting the scope thereof. Unless otherwise indicated, all parts, percents, ratios and the like are by weight.

EXAMPLE 1

7-[D-α-(4-Hydroxy-1,5-naphthyridine-3-carboxyamido)-α-phenylacetamido] cephalosporanic acid

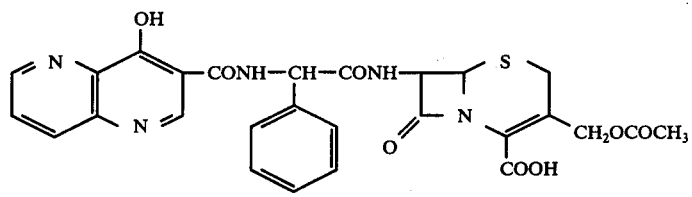

To a mixture of 12.16 g of 7-(D-α-amino-α-phenylacetamido) cephalosporanic acid, 6.0 g of triethylamine and 100 ml of dimethylsulfoxide were added 8.61 g of 4-hydroxy-1,5-naphthyridine-3-carboxylic acid N-hydroxy succinimide ester while stirring at room temperature. After the further addition of 50 ml of dimethylsulfoxide, stirring was continued for 1 hour at the same temperature. Then, after the addition of 5.5 g of sodium 2-ethylhexanoate to the reaction mixture, stirring was further continued for 20 minutes. A small amount of undissolved materials was filtered off and to the filtrate was added 1.5 l of acetone. The crystals which deposited were collected by filtration and washed with acetone and dried over phosphorus pentoxide under reduced pressure. Thus 9.62 g of the sodium salt of the titled compound was obtained (m.p. 240°-254° C (decomp.)).

The next day, 3.6 g of a second batch of crystals deposited.

EXAMPLE 2

7-[D-α-(4-Hydroxy-1,5-naphthyridine-3-carboxyamido)-α-phenylacetamido]-3-(2-methyl-1,3,4-thiadiazole-5-yl)thiomethyl-3-cephem-4-carboxylic acid

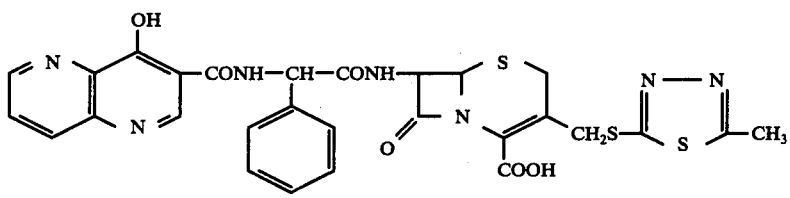

When an equivalent amount of 7-(D-α-amino-α-phenylacetamido)-3-(2-methyl-1,3,4-thiadiazole-5-yl)thiomethyl-3-cephem-4-carboxylic acid was substituted for the 7-(D-α-amino-α-phenylacetamido) cephalosporanic acid in Example 1, the titled compound was obtained (m.p. 240°-248° C (decomp.)).

EXAMPLES 3 and 4

In the same manner as in Example 1, the following compounds were synthesized.

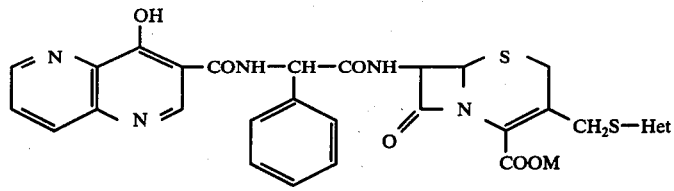

| Example No. | —Het | M | m.p. (decomp.) |
|---|---|---|---|
| 3 | ![triazole with N-CH3] | Na | 226 – 230° C |
| 4 | ![triazole N-H] | Na | 268 – 271° C |

EXAMPLE 5

7-[D-α-(4-Hydroxy-1,5-naphthyridine-3-carboxyamido)-α-phenylacetamido]-3-(1,2,3-triazole-5-yl)thiomethyl-3-cephem-4-carboxylic acid The titled compound (see Example 4) was also obtained by the following method.

To a mixture of 2.4 g of sodium 7-[D-α-(4-hydroxy-1,5-naphthyridine-3-carboxyamido)-α-phenylacetamido] cephalosporanate, 1.0 g of sodium bicarbonate, and 50 ml of a phosphate buffer (0.1N-KH$_2$PO$_4$ - 0.1N-NaHPO$_4$; 2 : 1 by volume; pH 6.4) at 60° C under a nitrogen atmosphere, 20 ml of an acetone solution which contained 1.2 g of 5-mercapto-1,2,3-triazole was added and stirring was continued for 5.5 hours. The crystals which deposited were collected by filtration and washed with ethanol and dried over phosphorus pentoxide under reduced pressure. Thus, 0.67 g of the titled compound was obtained and 0.72 g of a second batch of deposited crystals was obtained the next day.

Antibacterial Activity

The antibacterial activity in vitro and in vivo of cephalosporin derivatives of formula (I) against several organisms was compared with two cephalosporins as disclosed in Japanese patent application (OPI) Nos. 35,392/1974 and 82,687/1974, i.e., sodium 7-[D-α-(4-hydroxyquinoline-3-carboxyamino)-α-phenylacetamido] cephalosporanate (hereinafter referred to as "Compound (A)"):

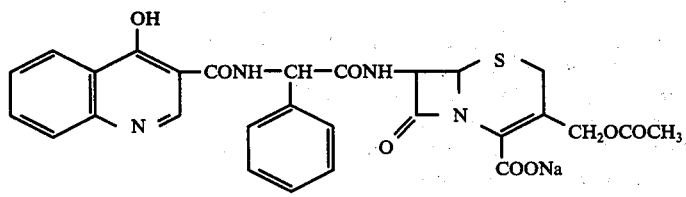

and sodium 7-[D-α-(4-hydroxypyridine-3-carboxyamino)-α-phenylacetamido] cephalosporanate (hereinafter referred to as "Compound (B)"):

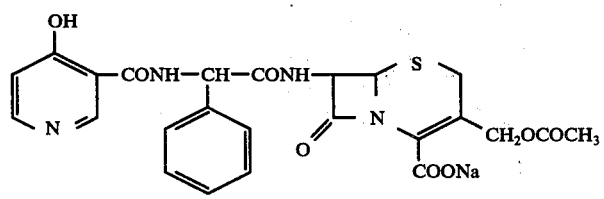

Minimum Inhibitory Concentrations

The minimum inhibitory concentrations obtained with the example compounds, Compound (A) and Compound (B), against the following organisms representing 6 genera are shown in Table 1.

TABLE 1

| | MIC (μg/ml) | | | | | |
|---|---|---|---|---|---|---|
| Compound | Escherichia coli NIHJ | Klebsiella pneumoniae PCI 602 | Proteus mirabilis GN 2425 | Pseudomonas aeruginosa T | Serratia No. 72 | Enterobacter aerogenes No. 75 |
| Example 1 | 3.13 | 1.56 | 12.5 | 6.25 | 50 | 6.25 |
| Example 2 | 1.56 | 0.78 | 12.5 | 6.25 | 12.5 | 3.13 |
| Example 3 | 0.78 | 0.39 | 12.5 | 12.5 | 12.5 | 3.13 |
| Example 4 | 1.56 | 1.56 | 25 | 12.5 | 25 | 3.13 |
| (A) | 6.25 | 0.78 | 25 | 12.5 | 100 | 25 |
| (B) | 12.5 | 12.5 | 50 | 25 | >200 | 25 |

MIC was determined by the nutrient broth dilution method.

As can be seen from Table 1, the antibacterial activities of the example compounds were superior to those of Compound (A) and Compound (B) against organisms such as Escherichia coli, Serratia and Enterobacter aerogenes.

Antibiotic Serum Concentrations

The antibiotic serum concentrations of the six cephalosporins following subcutaneous administration at 50 mg/kg to ICR-SLC strain mice are shown in Table 2.

It can be understood from Table 1 that the compounds of the present invention give higher serum levels than Compound (A).

TABLE 2

| Peak serum antibiotic concentrations and half-lives in mice | | | | | | |
|---|---|---|---|---|---|---|
| | Compound | | | | | |
| | Ex. No. 1 | Ex. No. 2 | Ex. No. 3 | Ex. No. 4 | (A) | (B) |
| Peak concentration (μg/ml) | 44 | 38 | 24 | 26 | <0.9 | 26 |
| t ½ (minutes) | 25 | 35 | 25 | 30 | — | 30 |

Note:
The bioassay was carried out according to the disc method using Pseudomonas aeruginosa.

Relative Activities

The relative activities of the compounds of the present invention, Compound (A) and Compound (B) against various intraperitoneal infections in mice evaluated by mean median protective doses (subcutaneously administered) are shown in Table 3.

TABLE 3

| | Test Organism | | | | | |
|---|---|---|---|---|---|---|
| | Escherichia coli No. 37 | | Pseudomonas aeruginosa T | Serratia No. 75 | | Enterobacter aerogenes No. 75 |
| Test Compound | MIC (μg/ml) | PD$_{50}$ (mg/kg) | PD$_{50}$ (mg/kg) | MIC (μg/ml) | PD$_{50}$ (mg/kg) | PD$_{50}$ (mg/kg) |
| Example 1 | 6.25 | 50 | 18 | 50 | 65 | 50 |
| Example 2 | 6.25 | 41 | 23 | 12.5 | 30 | 28 |
| Example 3 | 3.13 | 28 | 28 | 6.25 | 25 | 25 |
| Example 4 | 6.25 | 45 | 30 | 12.5 | 30 | 30 |
| (A) | 12.5 | >200 | >100 | 100 | >150 | >200 |
| (B) | 25 | 170 | 92 | >200 | >150 | 170 |

Note:
For each test, eight male ICR-SLC strain mice were used at each dose level.

MIC was determined by the nutrient broth dilution method.

PD$_{50}$ was observed with two subcutaneous treatments, i.e., 1 and 4 hours after infection.

It can be understood from Table 3 that the PD$_{50}$ values of the compounds of the present invention are markedly superior to those of Compounds (A) and (B).

From the above results, it can be understood that the compounds of the present invention promise higher protection in the treatment of various infectious diseases caused by gram-positive and gram-negative bacteria than various compounds of the prior art.

While the invention has been described in detail and with reference to specific embodiments thereof, it will be apparent to one skilled in the art that various changes and modifications can be made therein without departing from the spirit and scope thereof.

What is claimed is:

1. A compound of formula (I):

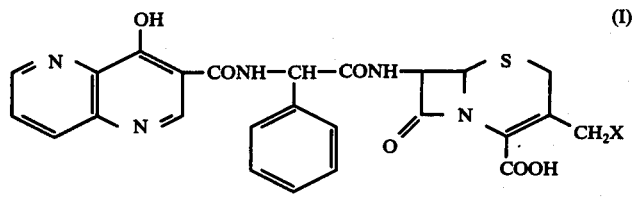

wherein X is an —S-Het group in which Het is a 5- or 6-membered heterocyclic ring containing 1 to 4 hetero atoms selected from the group consisting of nitrogen, oxygen and sulfur atoms which may be substituted with one or more substituents, and the non-toxic, pharmaceutically acceptable salts thereof.

2. The compound according to claim 1, wherein Het is 1-methyltetrazol-5-yl, 2-methyl-1,3,4-thiadiazol-5-yl, 1,2,3-triazol-5-yl, 1,2,4-triazol-3-yl, tetrazol-5-yl, 2-methyl tetrazole-5-yl, 2-mercapto-1,3,4-thiadiazol-5-yl, 2-hydroxymethyl-1,3,4-oxadiazol-5-yl, 2-hydroxymethyl-1,3,4-thiadiazol-5-yl, 2-aminomethyl-1,3,4-thiadiazol-5-yl, 3-hydroxypyridazin-6-yl, 1,3,4-thiadiazol-5-yl or 2-methylamino-1,3,4-thiadiazol-5-yl.

3. The compound of claim 1 having the formula:

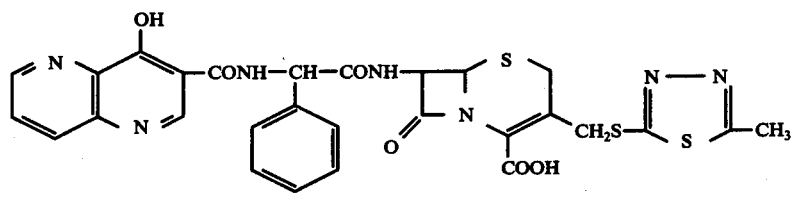

or non-toxic, pharmaceutically acceptable salts thereof.

4. The compound of claim 1 having the formula:

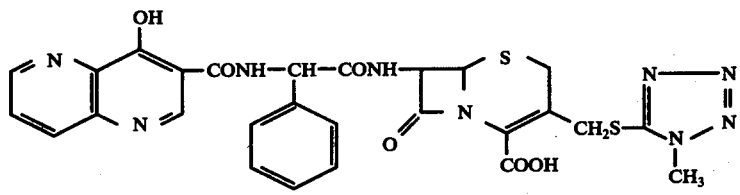

or non-toxic, pharmaceutically acceptable salts thereof.

5. The compound of claim 1 having the formula:

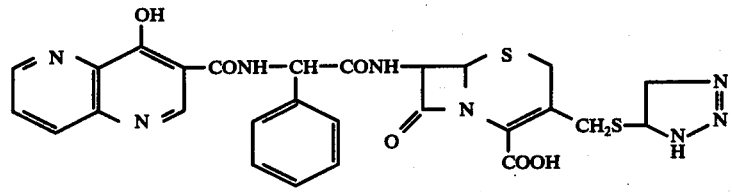

or non-toxic, pharmaceutically acceptable salts thereof.

6. An antimicrobial pharmaceutical composition which comprises a therapeutically effective amount of a compound of claim 1 or a non-toxic, pharmaceutically acceptable salt thereof and a pharmaceutically acceptable carrier or diluent.

* * * * *